United States Patent

Berneth et al.

[11] Patent Number: 5,866,353
[45] Date of Patent: Feb. 2, 1999

[54] ELECTRO CHEMICAL BIOSENSOR CONTAINING DIAZACYANINE MEDIATOR FOR CO-ENZYME REGENERATION

[75] Inventors: Horst Berneth, Leverkusen; Thomas Bocker, Leichlingen; Henry Giera, Bergisch-Gladbach, all of Germany; Alison J. Murray, Elkart, Ind.; Hans-Ulrich Siegmund, Cologne, Germany

[73] Assignee: Bayer Corporation, Elkart, Ind.

[21] Appl. No.: 762,098

[22] Filed: Dec. 9, 1996

[51] Int. Cl.[6] .............................. C12Q 1/32; G01N 27/26; C12M 1/00; C09B 44/10
[52] U.S. Cl. .............................. 435/26; 204/403; 435/25; 435/174; 435/287.1; 435/817; 534/607
[58] Field of Search ............................ 435/25, 26, 287.1, 435/174, 817; 204/403; 534/607

[56] References Cited

U.S. PATENT DOCUMENTS

| | | | |
|---|---|---|---|
| 4,710,570 | 12/1987 | Thien | 544/31 |
| 5,208,325 | 5/1993 | Berneth et al. | 534/607 |
| 5,436,323 | 7/1995 | Berneth et al. | 534/607 |
| 5,498,542 | 3/1996 | Corey et al. | 435/283.1 |
| 5,520,786 | 5/1996 | Bloczynski et al. | 264/403 |

*Primary Examiner*—David M. Naff
*Attorney, Agent, or Firm*—Jerome L. Jeffers

[57] ABSTRACT

A variety of diazacyanine mediators that are soluble in aqueous media and which do not inhibit enzymatic activity are provided for use on the surface of a working electrode of a electrochemical biosensor for electrochemical co-enzyme regeneration. The co-enzyme, dihydronicotinamide adenine dinucleotide (NADH) or dihydronicotinamide adenine dinucleotide phosphate (NADPH), is oxidized to $NAD^+$ OR $NADP^+$ which is reduced by an oxidoreductase such as a dehydrogenase acting on a substrate. By applying the mediator together with NADH or NADPH to the surface of the working electrode, the voltage necessary to achieve oxidation is substantially reduced. Biosensor electrodes such as graphite electrodes may be produced-by screen printing techniques.

10 Claims, 1 Drawing Sheet

ELECTRO CHEMICAL BIOSENSOR CONTAINING DIAZACYANINE MEDIATOR FOR CO-ENZYME REGENERATION

BACKGROUND OF THE INVENTION

A. Technical Summary:

The present invention relates to an enzyme electrode or an electrochemical biosensor which is suitable for the electrochemical determination of the concentration and/or for the survey of one of several components that may be present in a fluid test sample. As an enzyme system, generally every dihydronicotinamide adenine dinucleotide (NAD) or dihydronicotinamide adenine dinucleotide phosphate (NADP) dependent system can be considered. These systems combine the selectivity of enzymes with the sensitivity of amperometric detection and are of great interest to the diagnostics industry. The reduction of the nicotinamide co-enzymes (NAD and NADP) is particularly important because they are produced in reactions catalyzed by dehydrogenases. Dehydrogenase catalyzed reactions according to the equation:

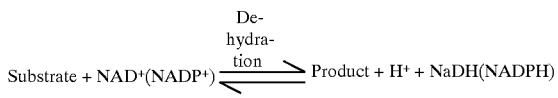

play an important role in biological cells and analytical reactions. Several hundred different dehydrogenases are known which Selectively catalyze the conversion of various substrates into products. When the substrate is oxidized, the coenzymes $NAD^+$ and $NADP^+$ are reduced to NADH and NADPH respectively. These co-enzymes are a necessary element in the reaction due to their ability to act with enzymes to form an energy transferring redox couple.

B. State of the Art:

A variety of reactions relevant to the field of biochemical analysis which use NAD(P) dependent oxireductases are at least in principle capable of being carried out through the use of such enzymes, cf. D. W. Moss et al in N. W. Tietz (Ed.), Textbook of Clinical Chemistry, Pp. 619–763, W. B. Saunders, Philadelphia, 1986. Generally, the change in the coenzyme, NAD(P)H concentration is determined by optical methods which can cause problems when colored or turbid samples are processed. As an alternative, electrochemical methods, in the form of biosensors, can be used.

It is known that the direct oxidation of NAD(P)H on an electrode surface requires a very high overpotential which leads to undesired phenomena such as electrode fouling or strong interference by contaminating substances. A number of publications and patents published in recent years have dealt with overcoming such problems, partly by the use of mediator molecules. The substances are initially reduced by NAD(P)H and then oxidatively regenerated in a second step at the anode. The use of a mediator facilitates the use of a lower electrochemical potential as compared to direct NAD (P)H oxidation. This is illustrated by the following equations:

  (1)

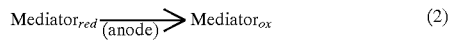  (2)

Examples for such mediators are often dyestuffs, like methylene blue, Meldola's Blue, Nile Blue, or Toluidine Blue [L. Gorton, J. Chem. Soc. Faraday Trans. 1, 82 (1986), 1245–1258]. These compounds often have the disadvantage that they themselves are reoxidized at such a high potential that all the relevant interferences are not always suppressed. In particular, in case of the determination of analytes in blood or urine, is it necessary to avoid the direct oxidation of ascorbic acid (Vitamin C), acetaminophen, bilirubin, and uric acid. This makes an oxidation potential in the range of 0 to 150 mV (versus silver/silver chloride reference) desirable. Furthermore, a high chemical turnover rate between NAD(P)H and the mediator as well as between mediator and the anode is desirable to obtain a sufficiently high current density. This aspect is crucial in particular for a desired miniaturization of biosensors and is not or only insufficiently covered by previously described mediators. The data of Table 8 herein demonstrate that the present mediator can meet this standard. In the case of a low turnover rate between NAD(P)H and mediator, there is observed an increase of the apparent oxidation potential in the presence of substrate. Furthermore, many of the prior art mediators are not sufficiently soluble in aqueous solution thereby necessitating the use of organic solvents and complex coating techniques for applying these mediators to an electrode. This limits the number of useable carrier materials for the biosensor, in particular in the field of polymers.

Accordingly, it would be desirable and it is an object of the present invention to provide mediators for the electrocatalytic oxidation of NADH or NADPH on carbon electrodes, particularly those produced by screen printing techniques. It is a further object of this invention to provide electrodes bearing the present mediators and NAD(P)H having an oxidation potential where current saturation occurs which is in the range of from 0 to 150 mV as measured against a silver/silver chloride reference electrode with the ability to obtain current densities on the order of 100 $\mu A/cm^2$ at 5 mmol/L NAD(P)H. In addition, it is an object of the present invention to provide mediators which are soluble in aqueous media and which do not inhibit enzymatic activity.

SUMMARY OF THE INVENTION

The objects of the present invention are met by the use of diazacyanines of Formula I:

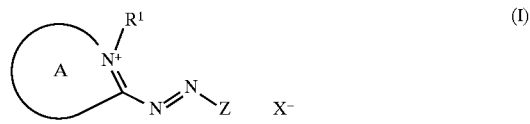  (I)

Referring to Formula I, A represents the remaining members of an aromatic or quasiaromatic 5 or 6 membered heterocyclic ring which can optionally be benzanellated;

$R^1$ is alkyl, alkenyl, alkinyl, cycloalkyl or aralkyl;

Z is the residue of a moiety of one of the formulae II, III or IV

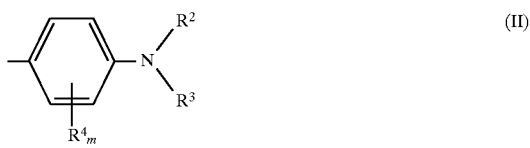  (II)

-continued

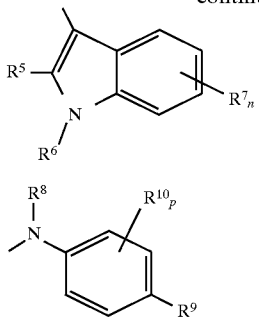
(III)

(IV)

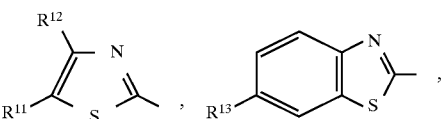

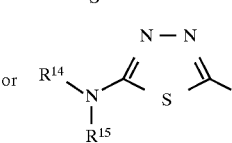

In the foregoing formulae:

$R^2$, $R^3$, $R^5$, $R^6$ and $R^8$ are independently hydrogen, alkyl, alkenyl, cycloalkyl, aralkyl, aryl or a saturated heterocyclic group; or $NR^2R^3$ is pyrrolidino, piperidino, morpholino, piperazino or N-alkylpiperazine or N-alkylpiperazino;

$R^4$ and $R^7$ are independently hydrogen, alkyl, alkoxy, halogen, hydroxy, nitro, cyano, alkanoylamino or alkylsulfonylamino; or $R^3$ and $R^4$ together are a —$CH_2CH_2$— or —$CH_2CH_2CH_2$— bridge which is optionally substituted with alkyl;

$R^9$ and $R^{10}$ are independently hydrogen, alkyl, alkoxy, halogen, hydroxy, nitro, cyano, alkanoyl or alkylsulfonyl;

m, n and p are independently 0, 1 or 2; and $X^-$ is an anion.

DETAILED DESCRIPTION OF THE INVENTION

Figure 1:
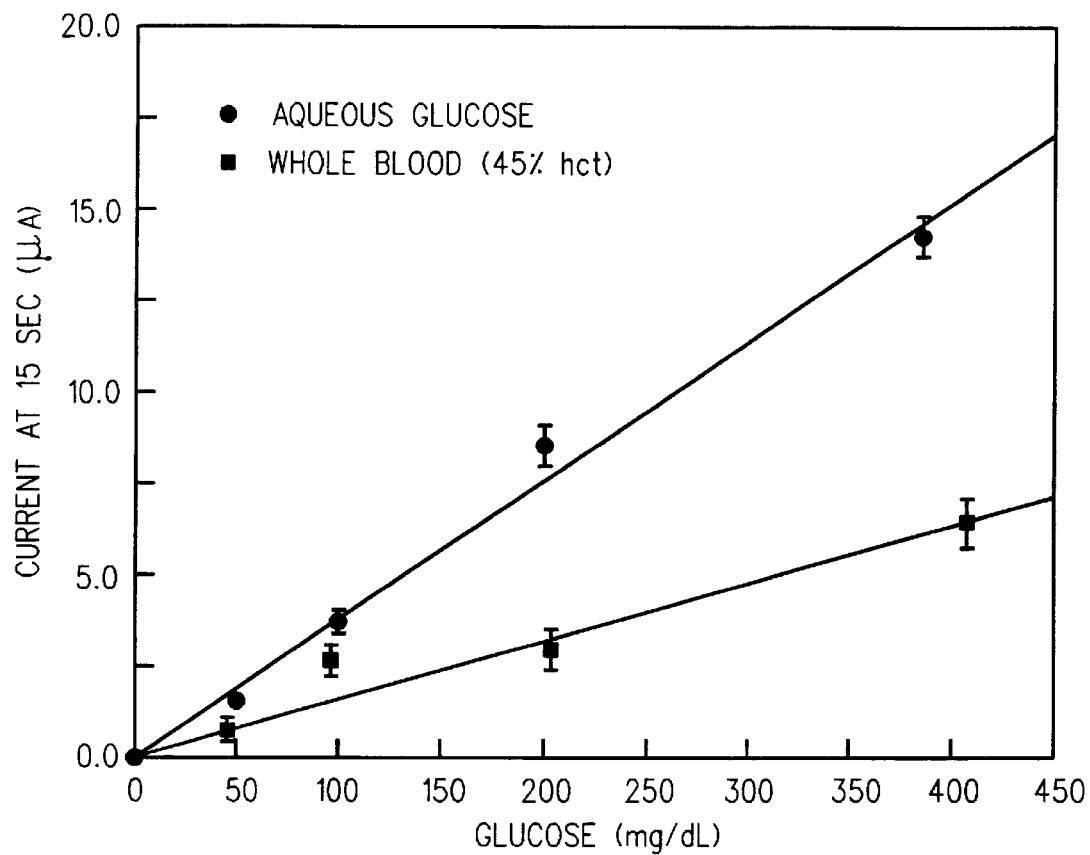
FIG. 1 shows measured response curves obtained by plotting currents against glucose concentration for an aqueous glucose solution and whole blood.

Referring to the above formula for the diazacyanines useful in the present invention, suitable counteranions ($X^-$) are any organic or inorganic anions which are not themselves redox-active in the range of working potentials of the electrical biosensor. Exemplary of anions which may be employed are chloride, tetrafluoroborate, hydrogensulfate, sulfate, dihydrogenphosphate, hydrogen phosphate, methylsulfate, ethylsulfate, acetate, phenylacetate, benzoate, methylsulfonate, benzenesulfonate and toluenesulfonate. If the anion used is polyvalent, such as sulfate or hydrogenphosphate, $X^-$ is one equivalent of such polyvalent anion.

According to the present invention, preferred diazacyanines for use as mediators are those in which the heterocycle is represented by the formula:

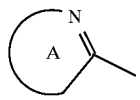
(V)

and is thiazole, benzothiazole, thiadiazole, pyrazole, indazole, imidazole, benzimidazole, triazole, pyridine, quinoline or pyrimidine or is represented by one of the formulae:

where $R^1$ is $C_1$ to $C_8$ alkyl, $C_3$ to $C_8$ alkenyl, $C_3$ to $C_8$ alkinyl, $C_4$ to $C_7$ cycloalkyl or $C_7$ to $C_9$ aralkyl which are unsubstituted or substituted with fluorine, chlorine, bromine, hydroxy, $C_1$ to $C_4$ alkyl, $C_1$ to $C_4$ alkoxy, cyano or $C_1$ to $C_4$ alkoxycarbonyl;

$R^2$, $R^3$, $R^5$, $R^6$, $R^8$, $R^{14}$ and $R^{15}$ are independently hydrogen, $C_1$ to $C_8$ alkyl, $C_3$ to $C_8$ alkenyl, $C_4$ to $C_7$ cycloalkyl, $C_7$ to $C_9$ aralkyl or $C_6$ to $C_{10}$ aryl which are unsubstituted or substituted with halogen, hydroxy, $C_1$ to $C_4$ alkyl, $C_1$ to $C_4$ alkoxy, cyano, $C_1$ to $C_4$ alkoxycarbonyl, $C_1$ to $C_4$ alkanoylamino, $C_1$ to $C_4$ alkylsulfonyl or tetramethysulfonyl;

$NR^2R^3$ and $NR^{14}R^{15}$ are independently pyrrolidino, piperidino or morpholino;

$R^4$ and $R^7$ are independently $C_1$ to $C_8$ alkyl; $C_1$ to $C_8$ alkoxy, hydroxy, fluoro, chloro, bromo, nitro, cyano, $C_1$ to $C_8$ alkanoylamino or $C_1$ to $C_8$ alkylsulfonylamino;

$R^3$ and $R^4$ together are a —$CH_2CH_2$— or —$CH_2CH_2CH_2$— bridge which is either unsubstituted or substituted with up to 3 methyl groups;

$R^9$ and $R^{10}$ are independently hydrogen, $C_1$ to $C_8$ alkyl, $C_1$ to $C_8$ alkoxy, hydroxy, fluoro, chloro, bromo, nitro, cyano, $C_1$ to $C_8$ alkanoyl or $C_1$ to $C_8$ alkylsulfonyl;

m, n and p are independently 0, 1 or 2;

$R^{11}$ and $R^{12}$ are independently hydrogen, $C_1$ to $C_8$ alkyl, $C_1$ to $C_8$ alkoxy, $C_4$ to $C_7$ cycloalkyl, $C_7$ to $C_9$ aralkyl, $C_6$ to $C_{10}$ aryl, fluoro, chloro, bromo or cyano;

$R^{13}$ is hydrogen, $C_1$ to $C_8$ alkyl, $C_1$ to $C_8$ alkoxy, fluoro, chloro, bromo or cyano; and $X^-$ is an anion wherein all of the alkyl, alkenyl, alkoxy and aralkyl groups are either straight chain or branched chain.

EXAMPLE I

Synthesis of Mediators

The preparation of the diazacyanines whose use as NAD (P)H mediators is the crux of the present invention is disclosed in U.S. Pat. No. 5,208,325 and U.S. Pat. No. 5,436,323 as well as U.S. Pat. No. 4,268,438 and U.S. Pat. No. 4,500,715 all of whose disclosures are incorporated herein by reference. The synthesis is described in detail in U.S. Pat. No. 5,208,325 in columns 5–8, particularly column 5, line 65 to column 6, line 28. In a manner analogous to this synthesis, one can use amino heterocycles of the formula:

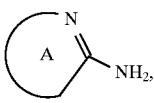

diazotize and couple to anilines or indoles of the formulae:

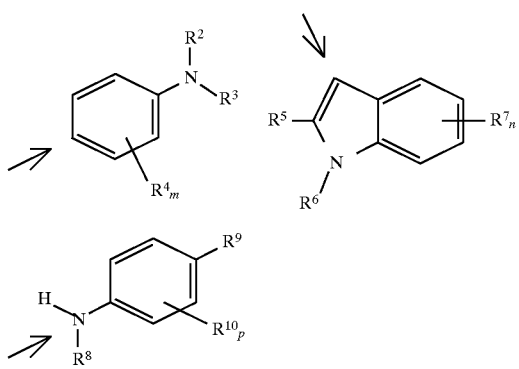

in the position marked with the arrow followed by quaternization with compounds of the formula:

$R^1X$ where X is a leaving group from which $R^1$ and $X^-$ in formula I are derived. This $R^1X$ can be, for example, methyl iodide, hydroxyethyl chloride or dimethyl sulfate. The conditions given in columns 7 and 8 for diazotization and quaternization may also be used.

EXAMPLE II

Evaluation of Mediators

Graphite rod electrodes (3 mm in diameter from Johnson Matthey Electronics, Ward Hill, Mass.) were prepared by contacting the rod with a silver wire, insulating all but the blunt end with heat shrink tubing after which the electrode's surface was polished with fine grit sandpaper followed by weigh paper. The electrode was immersed in a 1 mmol/L methanolic solution of the mediator to be tested immersed in 50 mL of phosphate buffer (25 mmol/L, pH 7.0). A cyclic voltammogram was run with 100 mV/sec. from —700 mV to +800 mV against a saturated calomel reference electrode. The anodic ($E_{ox}$) and cathodic $E_{(red)}$ peaks were determined. The results obtained using 38 representative compounds of the present invention are set out in Tables 1–6. From the data set out in Tables 1–6 it can be determined that the mediators tested meet the requirement of having a low oxidation potential to avoid electrochemical interference, while maintaining some reserve for system dependent shifts.

TABLE 1

| example | $R^1$ | $R^2$ | $R^3$ | $R^{4a}$ | $R^{4b}$ | $R^{13}$ | $X^-$ | $E_{ox}$/mV | $E_{red}$/mV |
|---|---|---|---|---|---|---|---|---|---|
| 1 | $CH_3$ | $CH_2CH_2CN$ | $CH_2CH_2CN$ | H | H | H | $Cl^-$ | −111 | −298 |
| 2 | $CH_3$ | $C_2H_5$ | $-C(CH_3)_2-CH_2-CH(CH_3)-$ | | H | H | $Cl^-$ | −235 | −498 |
| 3 | $CH_3$ | $C_2H_5$ | $C_2H_5$ | H | $NHSO_2CH_3$ | H | $Cl^-$ | −98 | −369 |
| 4 | $CH_3$ | $(CH_2)_2OCOCH_3$ | $(CH_2)_2OCOCH_3$ | H | H | H | $Cl^-$ | −142 | −635 |
| 5 | $CH_2CH_2CONH_2$ | $CH_3$ | —⟨Ph⟩—$OC_2H_5$ | H | H | H | $Cl^-$ | −218 | −515 |
| 6 | $CH_3$ | $-CH_2CH_2OCH_2CH_2-$ | | H | H | $OCH_3$ | $Cl^+$ | −44 | −551 |

TABLE 2

| example | $R^1$ | $R^2$ | $R^3$ | $R^{4a}$ | $R^{4b}$ | $R^{14}$ | $R^{15}$ | $X^-$ | $E_{ox}$/mV | $E_{red}$/mV |
|---|---|---|---|---|---|---|---|---|---|---|
| 7 | $CH_2CH_2CN$ | $CH_3$ | $CH_3$ | H | H | $CH(CH_3)_2$ | $CH(CH_3)_2$ | $ZnCl_3^-$ | −342 | −449 |
| 8 | $CH_3$ | $CH_3$ | $CH_3$ | H | H | $-(CH_2)_4-$ | | $CH_3OSO_3^-$ | −360 | −458 |
| 9 | $CH_3$ | $CH_3$ | $CH_3$ | H | H | $CH_2CH_2CN$ | $CH_2CH_2CN$ | $ZnCl_3^-$ | −311 | −435 |
| 10 | $CH_3$ | $CH_3$ | $CH_2-C_6H_5$ | H | H | $-CH_2CH(OH)CH_2$ | $-CH_2CH(OH)CH_3$ | $Cl^-$ | −302 | −440 |
| 11 | $CH_2CH_2CN$ | $CH_3$ | $CH_2CH_2CN$ | H | H | H | —⟨Ph⟩—CN | $Cl^-$ | −116 | −422 |

TABLE 2-continued

Structure: $R^{14}R^{15}N$-(1,3,4-thiadiazol-2,5-diyl)-N=N-phenyl(R^{4a}, R^{4b})-NR^2R^3$, $X^-$

| example | $R^1$ | $R^2$ | $R^3$ | $R^{4a}$ | $R^{4b}$ | $R^{14}$ | $R^{15}$ | $X^-$ | $E_{ox}$/mV | $E_{red}$/mV |
|---|---|---|---|---|---|---|---|---|---|---|
| 12 | $CH_3$ | $CH_3$ | $CH_3$ | H | H | H | 4-($NHCOCH_3$)$C_6H_4$- | $Cl^-$ | −289 | −445 |
| 13 | $CH_3$ | $CH_3$ | $CH_3$ | H | H | H | $-C_6H_5$ | $Cl^-$ | −289 | −462 |
| 14 | $CH_3$ | $CH_3$ | $CH_2CH_2CN$ | H | H | H | 3-($CN$)$C_6H_4$- | $Cl^-$ | −133 | −435 |
| 15 | $CH_3$ | $CH_3$ | $CH_3$ | H | H | H | 3-($CN$)$C_6H_4$- | $ZnCl_3^-$ | −200 | −475 |
| 16 | $CH_3$ | $CH_3$ | $CH_3$ | H | H | $CH_3$ | $-C_6H_5$ | $Cl^-$ | −298 | −435 |
| 17 | $CH_3$ | $CH_3$ | $CH_2CH_2CN$ | H | H | $CH_3$ | $CH_2CH_2CN$ | $ZnCl_3^-$ | −307 | −413 |
| 18 | $-CH_2CH(OH)CH_3$ | $CH_3$ | $CH_3$ | H | H | $CH(CH_3)_2$ | $CH(CH_3)_2$ | $ZnCl_3^-$ | −364 | −484 |
| 19 | $CH_3$ | $CH_3$ | $CH_2CH_2CN$ | H | H | $CH_2CH_2OH$ | cyclohexyl | $Cl^-$ | −311 | −422 |
| 20 | $-CH_2CH(OH)CH_3$ | $C_2H_5$ | $-CH_2C_6H_5$ | H | $CH_3$ | $CH(CH_3)_2$ | $CH(CH_3)_2$ | $ZnCl_3^-$ | −342 | −475 |
| 21 | $CH_3$ | H | $C_6H_5$ | $OCH_3$ | $NHCOCH_3$ | $-CH_2CH(OH)CH_3$ | $-CH_2CH(OH)CH_3$ | $ZnCl_3^-$ | −338 | −467 |
| 22 | $CH_3$ | $CH_3$ | $CH_3$ | H | H | H | 4-($OCH_3$)$C_6H_4$- | $Cl^-$ | −253 | −444 |
| 23 | $CH_3$ | $CH_3$ | $CH_3$ | $OCH_3$ | H | $CH_3$ | $CH_2CH_2CN$ | $ZnCl_3^-$ | −298 | −400 |
| 24 | $CH_3$ | $C_2H_5$ | $C_2H_5$ | H | $NHCOCH_3$ | $CH(CH_3)_2$ | $CH(CH_3)_2$ | $ZnCl_3^-$ | −431 | −507 |
| 25 | $(CH_2)_2CONH_2$ | $C_2H_5$ | $CH_2CH_2CN$ | H | H | H | 3-($CF_3$)$C_6H_4$- | $Cl^-$ | −239 | −364 |
| 26 | $CH_3$ | $CH_3$ | $CH_2CH_2CN$ | H | H | H | 4-($OC_2H_5$)$C_6H_4$- | $Cl^-$ | −178 | −409 |
| 27 | $CH_3$ | $CH_3$ | $CH_2CH_2CN$ | H | H | $CH_3$ | 4-($OCH_3$)$C_6H_4$- | $Cl^-$ | −253 | −408 |
| 28 | $CH_3$ | $C_2H_5$ | $CH_2CH_2CN$ | H | H | H | $C_6H_5$ | $Cl^-$ | −67 | −578 |
| 29 | $CH_3$ | $CH_3$ | $CH_3$ | H | H | $CH(CH_3)_2$ | $CH(CH_2)_2$ | $ZnCl_3^-$ | −364 | −490 |

TABLE 3

Structure: $R^{11}$, $R^{12}$ substituted thiazolium with $R^1$, N=N linker to phenyl($R^{4a}$, $R^{4b}$)-$NR^2R^3$, $X^-$

| example | $R^1$ | $R^2$ | $R^3$ | $R^{4a}$ | $R^{4b}$ | $R^{11}$ | $R^{12}$ | $X^-$ | $E_{ox}$/mV | $R_{red}$/mV |
|---|---|---|---|---|---|---|---|---|---|---|
| 30 | $CH_3$ | $CH_3$ | $CH_2CH_2CN$ | H | H | H | H | $Cl^-$ | −298 | −512 |
| 31 | $CH_3$ | $CH_2CH_2CN$ | $CH_2CH_2CN$ | H | $CH_3$ | H | $C_6H_5$ | $Cl^-$ | −250 | −468 |

TABLE 4 example | R¹ | R¹⁶ | R² | R³ | R⁴ᵃ | R⁴ᵇ | X⁻ | $E_{ox}$/mV | $E_{red}$/mV
---|---|---|---|---|---|---|---|---|---
32 | $CH_3$ | $CH_3$ | $CH_3$ | $CH_2C_6H_5$ | H | H | $ZnCl_3^-$ | −333 | −453
33 | $CH_3$ | $CH_3$ | $CH_2CH_2CN$ | $CH_2CH_2CN$ | H | H | $ZnCl_3^-$ | −279 | −405

TABLE 5 example | R¹ | R⁸ | R⁹ | R¹⁰ | R¹⁴ | R¹⁵ | X⁻ | $E_{ox}$/mV | $E_{red}$/mV
---|---|---|---|---|---|---|---|---|---
34 | $CH_3$ | $CH_3$ | $NO_2$ | H | $CH(CH_3)_2$ | $CH(CH_3)_2$ | $Cl^-$ | +27 | −289
35 | $CH_3$ | $CH_2CH_2CN$ | $CH_3$ | H | $CH(CH_3)_2$ | $CH(CH_3)_2$ | $Cl^-$ | +150 | −200
36 | $C_2H_5$ | $CH_3$ | CN | CN | $CH_3$ | $CH_3$ | $Cl^-$ | −36 | −270

TABLE 6 example | R¹ | R² | R³ | R⁴ᵃ | R⁴ᵇ | R¹⁷ | X⁻ | $E_{ox}$/mV | $E_{red}$/mV
---|---|---|---|---|---|---|---|---|---
37 | $CH_3$ | $C_2H_5$ | $-CH_2CH_6H_5$ | H | $CH_3$ | $CH_3$ | $Cl^-$ | −413 | −698
38 | $CH_3$ | $CH_3$ | $CH_3$ | H | $NHCOCH_3$ | $CH_3$ | $ZnCl_3^-$ | −420 | −623

EXAMPLE III

Cyclic Voltammograms of the Mediators

To measure the redox potentials, the substances to be tested were dissolved in water at a concentration of 2 mmol/L. On each of a series of screen printed carbon (graphite/carbon black mixture) electrodes (Acheson graphite ink, 3 mm² electrode surface activated by treatment in an oxygen plasma), 3 µL of this solution was applied and dried at room temperature. After 10 µL of phosphate buffer (25 mmol/L, pH 7.0) as physiological buffer was added, a cyclic voltammogram was run with 100 mV/sec. against a saturated Ag/AgCl reference electrode. Table 7 sets out the oxidation and reduction potentials which were obtained.

TABLE 7

Mediator | $E_{ox}$ [mV] | $E_{red}$ [mV]
---|---|---
17 | −123 | −448
19 | +29 | −477
14 | −270 | −434
27 | −190 | −404
43 | +92 | −70

From Table 7 it can be determined that the potentials are higher on printed electrodes than on graphite rod electrodes.

EXAMPLE IV

NADH Oxidation/Titration

In the same manner as described for the cyclic voltammetry experiment, printed graphite electrodes were coated with the particular mediator compound being tested. After connecting the treated electrode to a potentiostat, 10 μL of NADH of varying concentration (0, 2, 5 and 10 mmol/L) in phosphate buffer (25 mmol/L, pH 7.0) were added. A working potential was then applied against a saturated Ag/AgCl electrode, and the electrical current measured after 5 seconds. The currents were plotted versus NADH concentration, Table 8 shows the determined slopes at different working potentials for different mediators:

TABLE 8

| Mediator | Working Potential [mV] | Slope [μA/mM] |
|---|---|---|
| 17 | 200 | 0.060 |
| 10 | 100 | 0.15 |
|  | 300 | 0.36 |
| 9 | 100 | 0.17 |
| 14 | 100 | 0.23 |
|  | 300 | 0.24 |
| 27 | 100 | 0.31 |
|  | 300 | 0.36 |
| 43 | 100 | 0.14 |
|  | 300 | 0.40 |

From Table 8 it can be determined that the tested mediators demonstrate a high current density (0.2 μA/mM corresponds to 100 μA/cm² at 3 mm² electrode surface).

EXAMPLE V

Glucose Response Curve (Aqueous and Whole Blood)

A printed graphite electrode as used in Example III was coated with 3 μL of the following reagent solutions in which all percentages are w/v:

0.7% γ-Globulin 1.0% Polyvinyl pyrrolidone 0.1% Cremophor EL (surfactant)

0.85% NaCl 15 mmol/l NAD⁺

12 mM Mediator (17)

3.3 Units/μl Glucose dehydrogenase dissolved in 50 mM PIPES buffer, pH 7.0.

After the solution had dried at the electrode, it was connected to a potentiostat whereupon 10 μL of a solution with varying amounts of glucose (0 to 400 mg/dL) in phosphate buffer (25 mmol/L, pH 7.0) or in human blood (45% hematocrit) were added. The glucose concentration was adjusted by spiking it with a 25% aqueous solution and determining the actual concentration with a YSI STAT analyzer. The working potential was applied 15 seconds after applying the sample to a sensor and a current reading was taken after 5 seconds. The obtained currents were plotted against the glucose concentration. FIG. 1 shows the measured response curves for buffer solution and blood. From these response curves, it can be determined that an enzyme electrode made with the present mediators can be used to determine glucose in aqueous and blood solutions while leaving the enzyme activity intact.

I claim:

1. An electrode suitable for the electrochemical regeneration of the co-enzymes dihydronicotinamide adenine dinucleotide (NADH), dihydronicotinamide adenine dinucleotide phosphate (NADPH) or analogs thereof, said electrode having on its surface a mediator of Formula I:

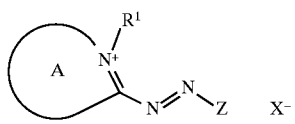

(I)

in which:

A represents the remaining members of an aromatic or quasiaromatic 5 or 6 membered heterocyclic ring which can be benzanellated;

R¹ is alkyl, alkenyl, alkinyl, cycloalkyl or aralkyl;

Z is the residue of a moiety of one of the formulae II, III or IV

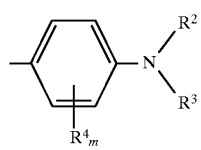

(II)

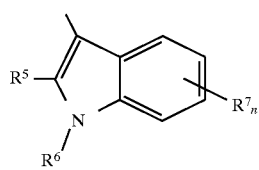

(III)

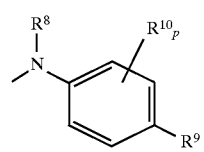

(IV)

wherein:

R², R³, R⁵, R⁶ and R⁸ are independently hydrogen, alkyl, alkenyl, cycloalkyl, aralkyl, aryl or a saturated heterocyclic group;

NR²R³ is pyrrolidino, piperidino, morpholino, piperazino or N-alkylpiperazine;

R⁴ and R⁷ are independently hydrogen, alkyl, alkoxy, halogen, hydroxy, nitro, cyano, alkanoylamino or alkylsulfonylamino;

R³ and R⁴ together are a —CH₂CH₂— or —CH₂CH₂CH₂— bridge which is substituted with alkyl;

R⁹ and R¹⁰ are independently hydrogen, alkyl, alkoxy, halogen, hydroxy, nitro, cyano, alkanoyl or alkylsulfonyl;

m, n and p are independently 0, 1 or 2; and

X⁻ is an anion.

2. The electrode of claim 1 in which

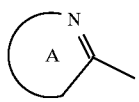

(V)

is thiazole, benzothiazole, thiadiazole, pyrazole, indazole, imidazole, benzimidazole, triazole, pyridine, quinoline or pyrimidine.

3. The electrode of claim 1 wherein the mediator is a cationic dyestuff of Formula I in which the heterocycle:

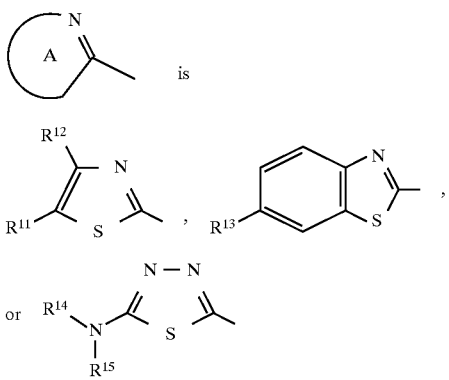

is

R¹ is $C_1$ to $C_8$ alkyl, $C_3$ to $C_8$ alkenyl, $C_3$ to $C_8$ alkinyl, $C_4$ to $C_7$ cycloalkyl or $C_7$ to $C_9$ aralkyl which are unsubstituted or substituted with fluorine, chlorine, bromine, hydroxy, $C_1$ to $C_4$ alkyl, $C_1$ to $C_4$ alkoxy, cyano or $C_1$ to $C_4$ alkoxycarbonyl;

$R^2$, $R^3$, $R^5$, $R^6$, $R^8$, $R^{14}$ and $R^{15}$ are independently hydrogen, $C_1$ to $C_8$ alkyl, $C_3$ to $C_8$ alkenyl, $C_4$ to $C_7$ cycloalkyl, $C_7$ to $C_9$ aralkyl or $C_6$ to $C_{10}$ aryl which are unsubstituted or substituted with halogen, hydroxy, $C_1$ to $C_4$ alkyl, $C_1$ to $C_4$ alkoxy, cyano, $C_1$ to $C_4$ alkoxycarbonyl, $C_1$ to $C_4$ alkanoylamino, $C_1$ to $C_4$ alkylsulfonyl or tetramethylsulfonyl;

$NR^2R^3$ and $NR^{14}R^{15}$ are independently pyrrolidino, piperidino or morpholino;

$R^4$ and $R^7$ are independently $C_1$ to $C_8$ alkyl; $C_1$ to $C_8$ alkoxy, hydroxy, fluoro, chloro, bromo, nitro, cyano, $C_1$ to $C_8$ alkanoylamino or $C_1$ to $C_8$ alkylsulfonylamino;

$R^3$ and $R^4$ together are a $-CH_2CH_2-$ or $-CH_2CH_2CH_2-$ bridge which is either unsubstituted or substituted with up to 3 methyl groups;

$R^9$ and $R^{10}$ are independently hydrogen, $C_1$ to $C_8$ alkyl, $C_1$ to $C_8$ alkoxy, hydroxy, fluoro, chloro, bromo, nitro, cyano, $C_1$ to $C_8$ alkanoyl or $C_1$ to $C_8$ alkylsulfonyl;

m, n and p are independently 0, 1 or 2;

$R^{11}$ and $R^{12}$ are independently hydrogen, $C_1$ to $C_8$ alkyl, $C_1$ to $C_8$ alkoxy, $C_4$ to $C_7$ cycloalkyl, $C_7$ to $C_9$ aralkyl, $C_6$ to $C_{10}$ aryl, fluoro, chloro, bromo or cyano;

$R^{13}$ is hydrogen, $C_1$ to $C_8$ alkyl, $C_1$ to $C_8$ alkoxy, fluoro, chloro, bromo or cyano; and X⁻ is an anion wherein all of the alkyl, alkenyl, alkoxy and aralkyl groups are either straight chain or branched chain.

4. The electrode of claim 1 in which the mediator has the formula:

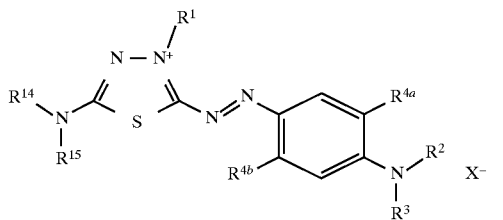

in which

R¹ means $C_1$- to $C_4$-alkyl, which is unsubstituted or substituted by fluorine, chlorine, hydroxy, methoxy, ethoxy, cyano, methoxycarbonyl or phenyl and which is branched or unbranched;

$R^2$, $R^3$, $R^{14}$ and $R^{15}$ independently of one another mean $C_1$- to $C_4$-alkyl, which is unsubstituted or substituted by fluorine, chlorine, hydroxy, methoxy, ethoxy, cyano, methoxycarbonyl or phenyl and which is branched or unbranched, cyclopentyl, cyclohexyl, tetramethylensulfon-3-yl or phenyl, which is unsubstituted or substituted by fluorine, chlorine, hydroxy, methyl, ethyl, methoxy, ethoxy, cyano, nitro, acetyl, methylsulfonyl or acetylamino, and $R^2$ and $R^{14}$ independently of one another may mean in addition hydrogen or $NR^2R^3$ and $NR^{14}R^{15}$ independently of one another mean pyrrolidino, piperidino or morpholino, $R^{4a}$ means hydrogen, fluoro, chloro, methyl or methoxy, $R^{4b}$ means hydrogen, fluoro, chloro, methyl, methoxy, cyano, nitro, hydroxy, acetylamino, propionylamino or methylsulfonylamino and X⁻ means an anion.

5. The electrode of claim 4 wherein:

R¹ means methyl, ethyl, hydroxyethyl, methoxyethyl, cyanoethyl or benzyl, $R^2$, $R^3$, $R^{14}$ and $R^{15}$ independently of one another mean methyl, ethyl, propyl, hydroxyethyl, hydroxypropyl, cyanoethyl, benzyl, cyclohexyl, phenyl, methylphenyl, methoxyphenyl, cyanophenyl or tetramethylensulfon-3-yl and $R^{14}$ additionally means hydrogen or $NR^2R^3$ and $NR^{14}R^{15}$ independently of one another mean pyrrolidino, piperidino or morpholino, $R^{4a}$ means hydrogen, methyl or methoxy, $R^{4b}$ means hydrogen, chloro, methyl, methoxy, cyano, acetylamino or methylsulfonylamino and X⁻ means an anion.

6. The electrode of claim 1 wherein the mediator has the formula:

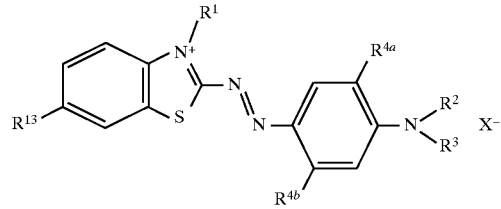

wherein:

R¹ means $C_1$- to $C_4$-alkyl, which is unsubstituted or substituted by fluorine, chlorine, hydroxy, methoxy, ethoxy, cyano, methoxycarbonyl or phenyl and which is optionally branched or unbranched, $R^2$ and $R^3$ independently of one another mean $C_1$- to $C_4$-alkyl, which is optionally unsubstituted or substituted by fluorine, chlorine, hydroxy, methoxy, ethoxy, cyano, methoxycarbonyl or phenyl and which is branched or unbranched, cyclopentyl, cyclohexyl, tetramethylensulfon-3-yl or phenyl, which is unsubstituted or substituted by fluorine, chlorine, hydroxy, methyl, ethyl, methoxy, ethoxy, cyano, nitro, acetyl, methylsulfonyl or acetylamino, and $R^2$ may mean in addition hydrogen or $NR^2R^3$ means pyrrolidino, piperidino or morpholino, $R^{4a}$ means hydrogen, fluorine, chlorine, methyl or methoxy, $R^{4b}$ means hydrogen, fluorine, chlorine, methyl, methoxy, cyano, nitro, hydroxy, acetylamino, propionylamino or methylsulfonylamino, $R^{13}$ means hydrogen, fluorine, chlorine, methyl, methoxy or ethoxy and $X^-$ means an anion.

7. The electrode of claim 6 wherein:

$R^1$ means methyl, ethyl, hydroxyethyl, methoxyethyl, cyanoethyl or benzyl, $R^2$ and $R^3$ independently of one another mean methyl, ethyl, propyl, hydroxyethyl, hydroxypropyl, cyanoethyl, benzyl, cyclohexyl, phenyl, methylphenyl, methoxyphenyl, cyanophenyl or tetramethylensulfon-3-yl or $NR^2R^3$ means pyrrolidino, piperidino or morpholino, $R^{4a}$ means hydrogen, methyl or methoxy, $R^{4b}$ means hydrogen, chlorine, methyl, methoxy, cyano, acetylamino or methylsulfonylamino, $R^{13}$ means hydrogen or methoxy and $X^-$ means an anion.

8. The electrode of claim 1 wherein the mediator has the formula:

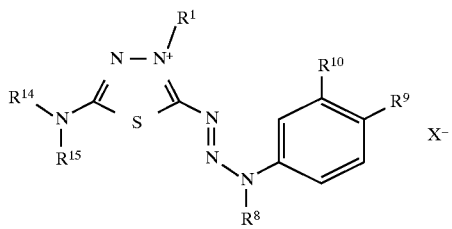

in which $R^1$ means $C_1$–$C_4$-alkyl, which is unsubstituted or substituted by fluorine, chlorine, hydroxy, methoxy, ethoxy, cyano, methoxycarbonyl or phenyl and which is optionally branched or unbranched, $R^8$ means $C_1$–$C_4$-alkyl, which is unsubstituted or substituted by fluorine, chlorine, hyddroxy, methoxy, ethoxy, cyano, methoxycarbonyl or phenyl and which is optionally branched or unbranched, cyclopentyl, cyclohexyl or phenyl, $R^9$ and $R^{10}$ independently mean hydrogen, fluorine, chlorine, methyl, methoxy, cyano, nitro, acetyl or methylsulfonyl, $R^{14}$ and $R^{15}$ independently mean $C_1$–$C_4$-alkyl, which is optionally unsubstituted or substituted by fluorine, chlorine, hydroxy, methoxy, ethoxy, cyano, methoxycarbonyl or phenyl and which is optionally branched or unbranched, cyclopentyl, cyclohexyl, tetramethylensulfon-3-yl or phenyl, which is optionally unsubstituted or substituted by fluorine, chlorine, hydroxy, methyl, ethyl, methoxy, ethoxy, cyano, nitro, acetyl, methylsulfonyl or acetylamino, $R^{14}$ may mean in addition hydrogen, $NR^{14}R^{15}$ means pyrrolidino, piperidino or morpholino and $X^-$ means an anion.

9. The electrode of claim 8 wherein:

$R^1$ means methyl, ethyl, hydroxyethyl, methoxyethyl, cyanoethyl or benzyl, $R^8$ means methyl, ethyl, hydroxyethyl, cyanoethyl or benzyl, $R^9$ means cyano, nitro, acetyl or methylsulfonyl, $R^{10}$ means hydrogen, chlorine, methyl or cyano, $R^{14}$ and $R^{15}$ independently of one another mean methyl, ethyl, propyl, hydroxyethyl, hydroxypropyl, cyanoethyl, benzyl, cyclohexyl, phenyl, methylphenyl, methoxyphenyl, cyanophenyl or tetramethylensulfon-3-yl and $R^{14}$ additionally means hydrogen or $NR^{14}R^{15}$ means pyrrolidino, piperidino or morpholino and $X^-$ means an anion.

10. A method of modifying the performance of an electrochemical biosensor having a working electrode and a reference electrode which operates with a dehydrogenase catalyst and a co-enzyme as an energy transferring redox couple, which method comprises using the electrode described in claim 1 as the working electrode of the biosensor.

* * * * *